United States Patent
Deych et al.

(10) Patent No.: US 10,539,687 B2
(45) Date of Patent: Jan. 21, 2020

(54) INDIRECT CONVERSION DETECTOR ARRAY

(71) Applicant: Analogic Corporation, Peabody, MA (US)

(72) Inventors: Ruvin Deych, Gloucester, MA (US); Andrew Litvin, Stoneham, MA (US); Vladan Ristanovic, Saugus, MA (US)

(73) Assignee: Analogic Corporation, Peabody, MA (US)

( * ) Notice: Subject to any disclaimer, the term of this patent is extended or adjusted under 35 U.S.C. 154(b) by 258 days.

(21) Appl. No.: 15/519,569

(22) PCT Filed: Oct. 16, 2014

(86) PCT No.: PCT/US2014/060844
§ 371 (c)(1),
(2) Date: Apr. 17, 2017

(87) PCT Pub. No.: WO2016/060667
PCT Pub. Date: Apr. 21, 2016

(65) Prior Publication Data
US 2017/0248705 A1 Aug. 31, 2017

(51) Int. Cl.
*A61B 6/03* (2006.01)
*A61B 6/00* (2006.01)
(Continued)

(52) U.S. Cl.
CPC ............ *G01T 1/2018* (2013.01); *A61B 6/032* (2013.01); *A61B 6/4208* (2013.01);
(Continued)

(58) Field of Classification Search
CPC .... A61B 6/032; A61B 6/4208; G01N 23/046; G01N 2223/501; G01N 2223/505; G01T 1/2018
See application file for complete search history.

(56) References Cited

U.S. PATENT DOCUMENTS 5,132,539 A 7/1992 Kwasnick et al.
7,054,408 B2 5/2006 Jiang et al.
(Continued)

FOREIGN PATENT DOCUMENTS

EP 0287707 A2 10/1988

OTHER PUBLICATIONS

Chinese Office Action and Search Report for Chinese Application No. 201480083456, dated Jan. 16, 2019, 20 pages with translation.
(Continued)

*Primary Examiner* — Mark R Gaworecki
(74) *Attorney, Agent, or Firm* — TraskBritt (57) ABSTRACT

Among other things, a detector array (300) for a radiation imaging system is provided. The detector array comprises a plurality of detector elements. Respective detector elements comprise, among other things, a scintillator (304) and a photodetector (306). In some embodiments, a scintillator is shared amongst two or more of the detector elements. In some embodiments, little to no reflective material, configured to mitigate cross-talk between detector elements, is situated between two or more detector elements.

20 Claims, 4 Drawing Sheets

(51) Int. Cl.
    *G01T 1/20*         (2006.01)
    *G01N 23/046*    (2018.01)

(52) U.S. Cl.
    CPC ..... *G01N 23/046* (2013.01); *G01N 2223/501* (2013.01); *G01N 2223/505* (2013.01)

(56) References Cited

U.S. PATENT DOCUMENTS

| | | |
|---|---|---|
| 2010/0270462 A1 | 10/2010 | Nelson et al. |
| 2011/0180714 A1* | 7/2011 | Okada .................. G01T 1/243 250/354.1 |
| 2012/0056104 A1* | 3/2012 | Perna .................. G01T 1/2002 250/486.1 |

OTHER PUBLICATIONS

The State Intellectual Property Office of People's Republic of China (SIPO), The First Office Action dated Jul. 20, 2018 in co-pending CN Application No. 201480083456.7 having a filing date of May 16, 2017 (9 pgs).
International Search Report cited in related application No. PCT/US14/60844 dated Jun. 23, 2015, pp. 11
CN Office Action dated Aug 27, 2019 for CN Application No. 201480083456, 37 pages.

\* cited by examiner

INDIRECT CONVERSION DETECTOR ARRAY

TECHNICAL FIELD

The present disclosure relates to an indirect conversion detector array of a radiation imaging system. It finds particular application in medical, security, and/or industrial fields, where radiation imaging systems are used to identify/view interior aspects of an object under examination.

BACKGROUND

Today, radiation imaging systems such as computed tomography (CT) systems, digital projection systems, and/or line-scan systems, for example, are useful to provide information, or images, of interior aspects of an object under examination. The object is exposed to rays of radiation photons (e.g., x-ray photons, gamma ray photons, etc.) and radiation photons traversing the object are detected by a detector array positioned substantially diametrically opposite a radiation source relative to the object. A degree to which the radiation photons are attenuated by the object (e.g., absorbed, scattered, etc.) is measured to determine one or more properties of the object, or rather aspects of the object. For example, highly dense aspects of the object typically attenuate more radiation than less dense aspects, and thus an aspect having a higher density, such as a bone or metal, for example, may be apparent when surrounded by less dense aspects, such as tissue or clothing.

Detector arrays comprise a plurality of detector elements, respectively configured to detect radiation impinging a predefined portion of the detector array. The detector elements are configured to directly or indirectly convert radiation photons into electrical charge. Direct conversion detector elements are configured to convert the radiation photons directly into electrical charge using a photoconductor (e.g., amorphous selenium). Indirect conversion detector elements are configured to convert the radiation photons into light using a scintillator and to convert the light into electrical charge using a photodetector, such as a photodiode. In a detector array comprising indirect conversion detector elements, conventional detector elements do not share a same scintillator and do not share a same photodetector. For example, a first scintillator of a first detector element and a second scintillator of an adjacent detector element are separated by a reflective material configured to mitigate light generated in the first scintillator from being transferred to the second detector element. In this way, optical cross-talk between detector elements is mitigated, for example.

BRIEF SUMMARY

Aspects of this disclosure address the above matters, and others. According to one aspect, a detector array is provided. The detector array comprises a scintillator configured to generate luminescent photons responsive to a detection event. The detector array also comprises a plurality of photodetectors situated proximate an underside of the scintillator and configured to detect at least some of the luminescent photons. The scintillator is substantially continuously distributed over at least two photodetectors of the plurality.

According to another aspect, a detector array is provided. The detector array comprises a scintillator configured to generate luminescent photons responsive to a detection event. The detector array also comprises a plurality of photodetectors situated proximate an underside of the scintillator and configured to detect at least some of the luminescent photons. The scintillator is shared between at least two photodetectors of the plurality.

According to another aspect, a radiation imaging system is provided. The radiation imaging system comprises a radiation source configured to emit radiation photons and a detector array comprising a plurality of detector elements. A first detector element of the plurality comprises a first portion of a shared scintillator and a first photodetector situated proximate an underside of the first portion. A second detector element of the plurality comprises a second portion of the shared scintillator and a second photodetector situated proximate an underside of the second portion.

Those of ordinary skill in the art will appreciate still other aspects of this disclosure upon reading and understanding the appended description.

BRIEF DESCRIPTION OF THE FIGURES

This disclosure is illustrated by way of example and not limitation in the figures of the accompanying drawings, in which like references indicate similar elements and in which.

DETAILED DESCRIPTION

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

According to some embodiments, an indirect conversion detector array is provided. The indirect conversion detector array comprises a scintillator that is shared between two or more detector elements. For example, a first detector element comprises a first portion of a shared scintillator and a first photodetector. A second detector element comprises a second portion of the shared scintillator and a second photodetector. Accordingly, given that the scintillator is a shared scintillator, in some embodiments, there is no reflective material between the first detector element and the second detector element. Further, because the first detector element and the second detector element share a scintillator, there may be few, if any, dice lines in the scintillator between the first photodetector and the second photodetector.

Figure 1:
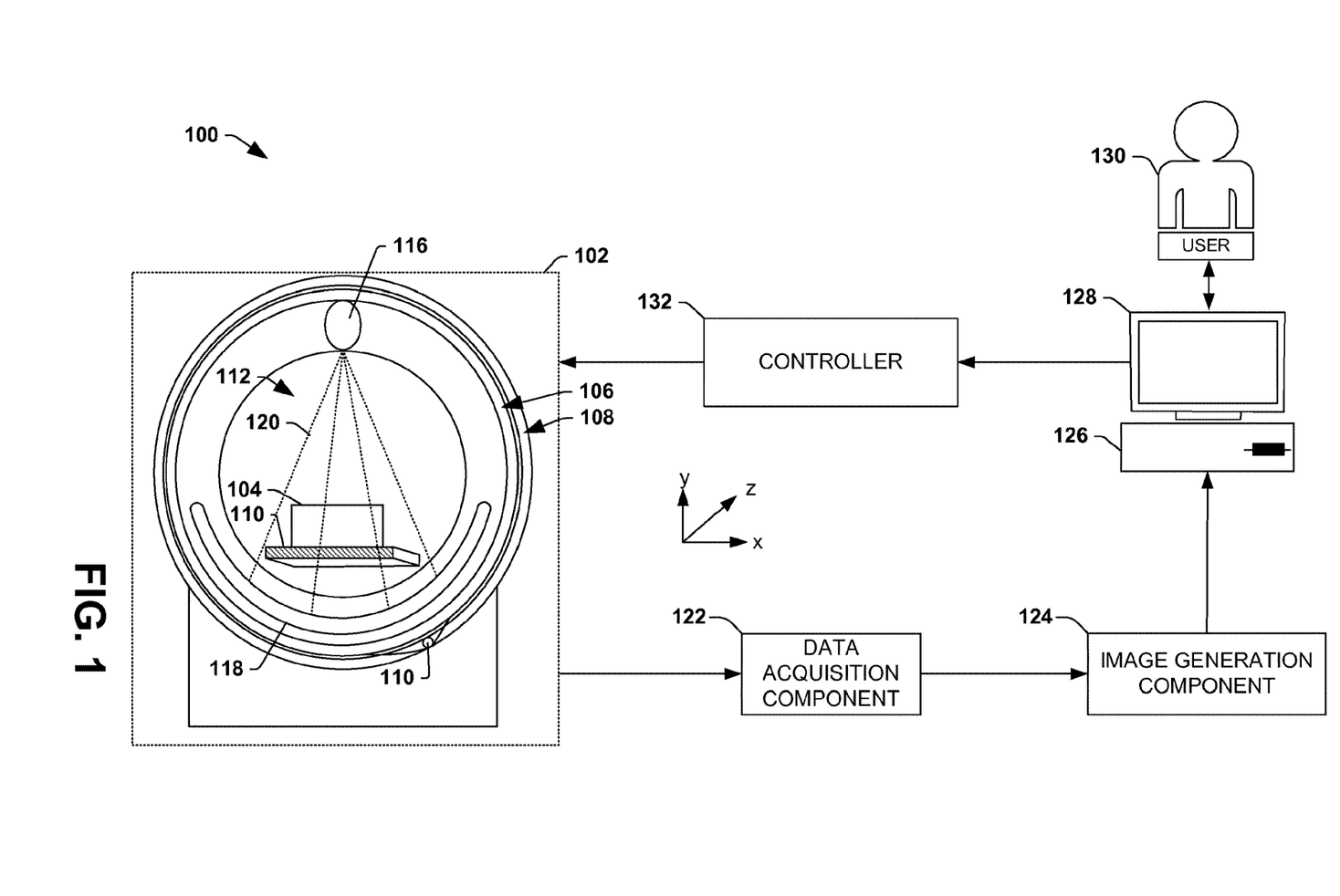
FIG. 1 is a schematic block diagram illustrating an example radiation imaging system.

FIG. 1 illustrates a radiation imaging system 100 where the techniques and/or systems described herein may be employed. In the illustrated embodiment, the radiation imaging system 100 is a computed tomography (CT) system, although the systems and/or techniques described herein may find applicability to other radiation imaging systems such as line-scan systems, mammography systems, and/or diffraction systems, for example. The radiation imaging system 100 thus merely provides an example arrangement and is not intended to be interpreted in a limiting manner, such as necessarily specifying the location, inclusion, and/or relative position of the components depicted therein. By way of example, in some embodiments, a data acquisition component 122 (also regarded as a data acquisition system (DAS)) is part of a detector array 118 and/or is located on a rotating gantry 106 of an examination unit 102.

In the example radiation imaging system 100, the examination unit 102 is configured to examine objects 104 (e.g., suitcases, cargo, patients, etc.). The examination unit 102 comprises the rotating gantry 106 and a (stationary) support structure 108 (e.g., which may encase and/or surround at least a portion of the rotating gantry 106 (e.g., as illustrated with an outer, stationary ring, surrounding an outside edge of an inner, rotating ring)). During an examination of an object 104, the object 104 is placed on a support article 110, such as a bed or conveyor belt, for example, and positioned within an examination region 112 (e.g., a hollow bore in the rotating gantry 106), where the object 104 is exposed to radiation 120.

The rotating gantry 106 may surround a portion of the examination region 112 and may comprise a radiation source 116 (e.g., an ionizing radiation source such as an x-ray source and/or gamma-ray source) and the detector array 118. The detector array 118 is typically mounted on a substantially diametrically opposite side of the rotating gantry 106 relative to the radiation source 116, and during an examination of the object 104, the rotating gantry 106 (e.g., including the radiation source 116 and detector array 118) is rotated about the object 104. Typically, a plane in which the rotating gantry 106 is rotated is defined as an x,y plane and a direction in which the object is translated into and out of the examination region 112 is referred to as the z-direction. Because the radiation source 116 and the detector array 118 are mounted to the rotating gantry 106, a relative position between the detector array 118 and the radiation source 116 is substantially maintained during the rotation of the rotating gantry 106.

During the examination of the object 104, the radiation source 116 emits cone-beam and/or fan-beam radiation configurations from a focal spot of the radiation source 116 (e.g., a region within the radiation source 116 from which radiation 120 emanates) into the examination region 112. Such radiation 120 may be emitted substantially continuously and/or may be emitted intermittently (e.g., a brief pulse of radiation 120 is emitted followed by a resting period during which the radiation source 116 is not activated). Further, the radiation 120 may be emitted at a single energy spectrum or at multiple energy spectrums depending upon, among other things, whether the radiation imaging system 100 is configured as a single-energy system or a multi-energy (e.g., dual-energy) system.

As the emitted radiation 120 traverses the object 104, the radiation 120 may be attenuated differently by different aspects of the object 104. Because different aspects attenuate different percentages of the radiation 120, the number of photons and/or energy levels of respective photons detected by detector elements of the detector array 118 may vary. For example, more dense aspects of the object(s) 104, such as a bone, may attenuate more of the radiation 120 (e.g., causing fewer photons to impinge upon a region of the detector array 118 shadowed by the more dense aspects) than less dense aspects, such as tissue.

The detector array 118 comprises a plurality of detector elements respectively configured to convert radiation photons impinging the detector element into electrical charge to produce analog signals. In some embodiments, the detector array 118 is a one-dimensional array, where the detector array 118 comprises a plurality of columns of detector elements (e.g., extending in the x,y plane) and a single row of detector elements (e.g., extending in the z-direction, which goes into the page in FIG. 1). In other embodiments, the detector array 118 is a two-dimensional array, where the detector array 118 comprises a plurality of columns of detector elements and a plurality of rows of detector elements.

The detector elements respectively comprise a scintillator configured to generate light (e.g., luminescent photons within a visible light wavelength spectrum) responsive to a radiation photon interacting with the scintillator and a photodetector (e.g., photodiode) configured to generate electrical charge based upon light detected by the photodetector. As will be further described below, at least some of the detector elements share a scintillator. For example, the scintillator may be substantially continuously distributed over at least two detector elements without an intervening non-scintillating element. By way of example, there may be no reflective material separating a first portion of the scintillator above a first photodetector of a first detector element from a second portion of the scintillator above a second photodetector of a second detector element. In some embodiments, the scintillator maintains a substantially uniform composition between the first detector element and the second detector element with which the scintillator is shared.

The analog signals that are generated by respective detector elements of the detector array 118 can be transmitted from the detector array 118, or from the photodetectors of the detector array 118, to the data acquisition component 122 operably coupled to the detector array 118. The data acquisition component 122 may be an integral part of the detector array 118 or may be a separate electronic package that is connected to the detector array 118 via an electrical connection. The analog signal(s) may carry information indicative of the radiation detected by the detector array 118 (e.g., such as an amount of charge measured over a sampling period and/or an energy level of detected radiation).

The data acquisition component 122 is configured to amplify and/or convert the analog signals output by the detector array 118 into digital signals (e.g., digitizing the electrical charge produced by the photodetectors and/or digitizing a current generated from the electrical charge to produce a digital output) and/or to compile signals that were transmitted within a predetermined time interval, or measurement interval, using various techniques (e.g., integration, photon counting, etc.). The compiled signals are typically in projection space and are, at times, referred to as projections. A projection may be representative of the information collected or measurements acquired by respective detector elements of the detector array 118 during an interval of time or a view, where a view corresponds to data collected while the radiation source 116 was at a particular view-angle or within a particular angular range relative to the object 104.

Data (e.g., the digital signals and/or the projections) generated by the data acquisition component 122 may be transmitted to an image generation component 124 operably coupled to the data acquisition component 122. The image generation component 124 is configured to convert at least some of the data from projection space to image space using suitable analytical, iterative, and/or other reconstruction techniques (e.g., tomosynthesis reconstruction, back-projection, iterative reconstruction, etc.). The images generated by the image generation component 124 may be in two-dimensional space and/or three-dimensional space and may be representative of the degree of attenuation through various aspects of the object 104 for a given view, may be representative of the density of various aspects of the object 104, and/or may be representative of the effective atomic number of various aspects of the object 104, for example.

The example radiation imaging system 100 further comprises a terminal 126, or workstation (e.g., a computer), that may be configured to receive images output by the image generation component 124, which may be displayed on a monitor 128 to a user 130 (e.g., security personnel, medical personnel, etc.). In this way, the user 130 can inspect the image(s) to identify areas of interest within the object 104, for example. The terminal 126 can also be configured to receive user input that can direct operations of the examination unit 102 (e.g., a speed to rotate, a speed and direction of the support article 110, etc.), for example.

In the example radiation imaging system 100, a controller 132 is operably coupled to the terminal 126. The controller 132 may be configured to control operations of the examination unit 102, for example. By way of example, in one embodiment, the controller 132 may be configured to receive information from the terminal 126 and to issue instructions to the examination unit 102 indicative of the received information (e.g., change the position of the support article relative to the radiation source 116, etc.).

Figure 2:
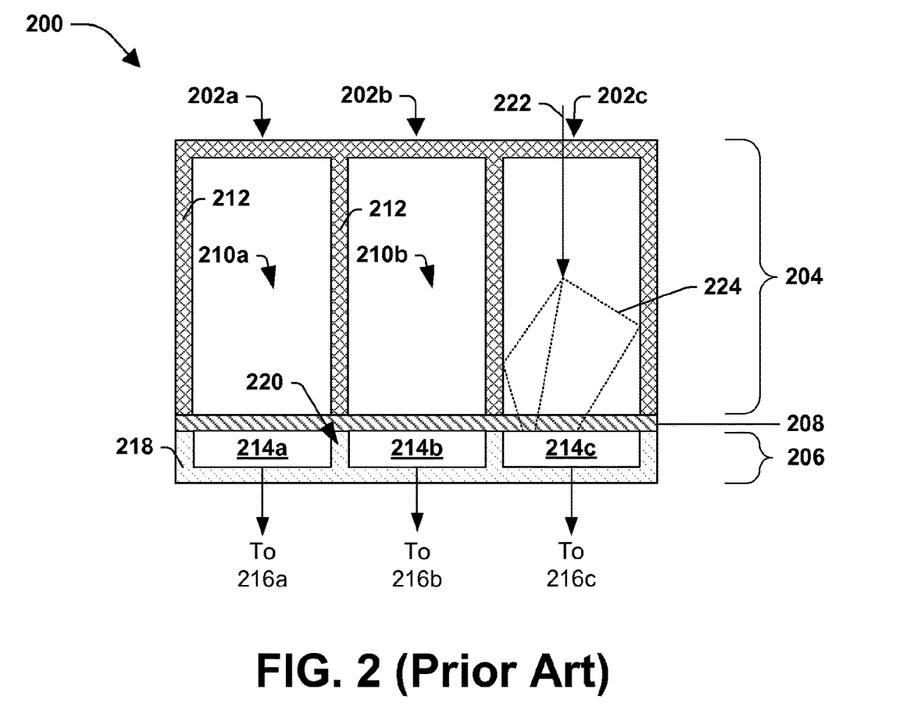
FIG. 2 is a cross-sectional view of a conventional detector array.

FIG. 2 illustrates a cross-sectional view of a conventional indirect conversion detector array 200. The detector array 200 comprises a conversion layer 204, a photodetector layer 206, and an adhesion layer 208 for bonding or otherwise coupling the conversion layer 204 to the photodetector layer 206. The conversion layer 204 comprises scintillators 210a and 210b (collectively referred to herein as scintillators 210) and reflective material 212. The photodetector layer 206 comprises photodetectors 214a, 214b or 214c (collectively referred to herein as photodetectors 214), which are operably coupled (e.g., electrically coupled) to data acquisition channels 216a-c (collectively referred to herein as data acquisition channels 216) of the data acquisition component 122. In some embodiments the photodetectors 214 are silicon p-i-n photodiodes, which can be discreet photodiode elements on a substrate 218, or active photodiode areas created in a monolithic silicon wafer. A gap 220 is defined between the discreet photodiodes or is defined at inactive areas in the silicon wafer. In some embodiments, the photodetectors 214 and the data acquisition channels 216 can be integrated in modules, or tiles, to reduce a connection wire path, for example.

The conversion layer 204 and the photodetector layer 206 are dissected into detector elements 202a and 202b (collectively referred to herein as detector elements 202). Respective detector elements 202 comprise one scintillator 210 and one photodetector 214. Accordingly, a first detector element 202a comprises a first scintillator 210a and a first photodetector 214a. Likewise, a second detector element 202b comprises a second scintillator 210b and a second photodetector 214b. Typically, the first scintillator 210a is bonded, at a dice line of the first scintillator 210a (e.g., the dice line running vertically on the page), to the second scintillator 210b, at a dice line of the second scintillator 210b (e.g., also running vertically on the page) via the reflective material 212.

Conventionally, the scintillator 210 of respective detector elements 202 is separated from other scintillators 210 of other detector elements 202 by the reflective material 212.

For example, the first scintillator 210a is separated from the second scintillator 210b by reflective material 212, which is typically positioned above the gap 220 defined between the first photodetector 214a and the second photodetector 214b.

When a radiation photon 222 impinges (e.g., interacts with) a scintillator 210 of a detector element 202 (e.g., referred to herein as a detection event), the scintillator 210 generates luminescent photons 224 that are distributed through the scintillator 210. At least some of the luminescent photons 224 may interact with and/or be reflected by the reflective material 212 (e.g., as shown in FIG. 2 with luminescent photons 224 being reflected back into the scintillator 210 by the reflective material 212). In this way, most, if not all, of the luminescent photons 224 generated within a detector element 202 remain trapped within the detector element 202 in which the luminescent photons 224 were generated and are detected by a photodetector 214 of the detector element 202 in which the luminescent photons 224 were generated.

Photodetectors 214 are configured to generate electrical charge in response to being exposed to light (e.g., based upon the photovoltaic effect of the photodetector 214 (e.g., the photovoltaic effect of the silicon photodiode)). If the energy of the luminescent photons 224 is greater than a bandgap energy of the photodetector 214, electrons in the photodetector 214 will move from a valence band onto a conduction band, and electron-hole pairs will be generated. Free electrons and holes generated within a depletion layer of the photodetector 214 may drift in an internal field in opposite directions and therefore induce an electric current in an external circuit. The electric current is sampled during a readout time period by a corresponding data acquisition channel 216 to create a digital output, or view. The data acquisition channel 216 can be of single photon counting (SPC) type or energy integrating type. In the former, the digital output may comprise information about a number of detected radiation photons and in the latter, the digital output may be proportional to radiation energy detected over the sampling time interval.

Figure 3:
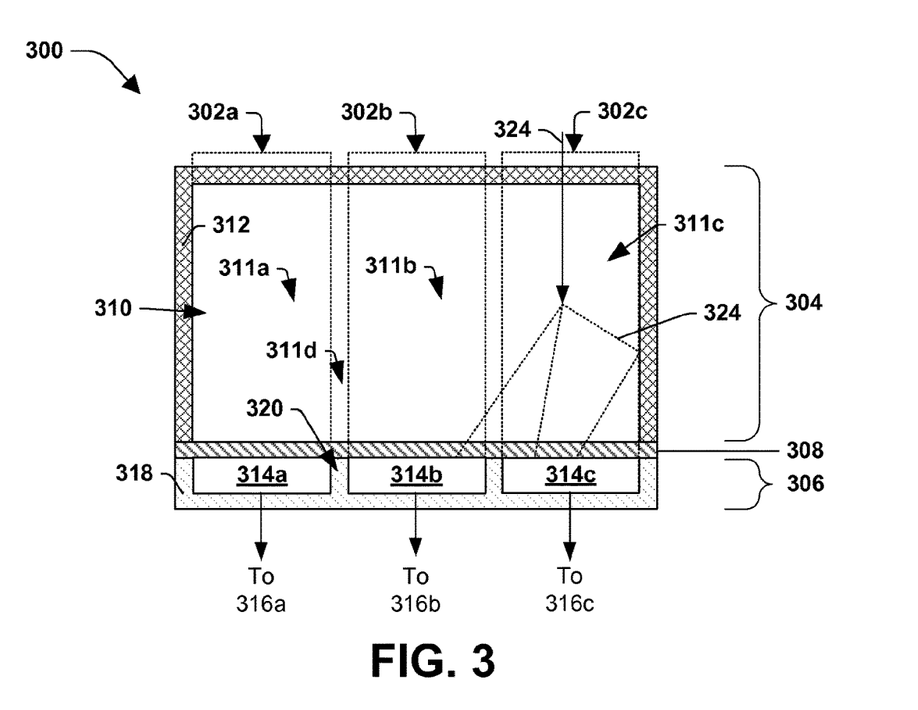
FIG. 3 is a cross-section view of a detector array comprising a shared scintillator.

Referring to FIG. 3, a cross-sectional view of an indirect conversion detector array 300 according to some embodiments (e.g., 118 in FIG. 1) is illustrated. The detector array 300 comprises a conversion layer 304, a photodetector layer 306, and an adhesion layer 308 for bonding or otherwise coupling the conversion layer 304 to the photodetector layer 306. The conversion layer 304 comprises one or more scintillators 310a or 310b (collectively referred to herein as scintillators 310) and reflective material 312.

The photodetector layer 306 comprises photodetectors 314a, 314b and 314c (collectively referred to herein as photodetectors 314) operably coupled (e.g., electrically coupled) to the data acquisition channels 316a-c (collectively referred to herein as data acquisition channels 316) of the data acquisition component 122. In some embodiments, the photodetectors 314 and the data acquisition channels 316 can be integrated in modules, or tiles, to reduce a connection wire path, for example.

A plurality of detector elements 302a and 320b (collectively referred to herein as detector elements 302) are formed within the indirect conversion detector array 300. For purposes of illustration, dotted rectangles in FIG. 3 represent the boundaries of respective detector elements, where the boundaries are defined based upon boundaries of the photodetectors 314. In some embodiments, the detector elements 302 are arranged in a grid-like arrangement forming one or more columns (e.g., extending in the x,y plane) and/or one or more rows (e.g., extending in the z-direction).

In other embodiments, the detector elements 302 are arranged according to other random or non-random arrangements (e.g., a honey-comb arrangement).

Respective detector elements 302 comprise a scintillator 310 and a photodetector 314 situated proximate an underside of the scintillator 310. In some embodiments, a scintillator 310 is shared between detector elements 302. A scintillator 310 shared between two or more detector elements is, at times, referred to as a shared scintillator because the scintillator overlays at least two photodetectors 314 (e.g., of two detector elements 302) and is thus shared between the detector elements 302. For example, a first detector element 302a comprises a first portion 311a of a shared scintillator 310 and a first photodetector 314a, which is operably coupled to a first data acquisition channel 316a. As another example, a second detector element 302b comprises a second portion 311b of a shared scintillator 310 and a second photodetector 314b, which is operably coupled to a second data acquisition channel 316b. As yet another example, a third detector element 302c comprises a third portion 311c of a shared scintillator 310 and a third photodetector 314c, which is operably coupled to a third data acquisition channel 316c.

Due to the shared nature of the scintillator 310, the scintillator 310 is substantially continuously distributed over the first photodetector 314a, the second photodetector 314b, and the third photodetector 314c. For example, there are no dice lines between the first portion 311a of the scintillator 310 and the second portion 311b of the scintillator 310. Further, in contrast to the detector array 200 illustrated in FIG. 2, a region of the conversion layer 304 above a gap 320 between the first photodetector 314a and the second photodetector 314b comprises a scintillator as opposed to reflective material, and thus the scintillator 310 is substantially continuously distributed over, among other things, the first photodetector 314a, the gap 320, and the second photodetector 314b, for example.

The scintillator 310 can comprise a phosphor screen, a ceramic material (e.g., Gadolinium Oxysulfide (GOS), doped with Praseodymium (Pr), Terbium (Tb), or other activators.), and/or other scintillating material. In some embodiments, the scintillator 310 comprises an optically translucent ceramic scintillator material (e.g., GOS). Due to the anisotropic nature of GOS material, luminescent light scatters on grain boundaries of the GOS material, which increases light absorption. As a consequence a lateral transmission (e.g., left-to-right on the page) of the luminescent photons 324 is reduced, and a lateral attenuation of the luminescent light creates a narrow spread function without the use of physical channel separation, for example. In some embodiments, the scintillating material is configured to generate luminescent photons in the visible spectral range, having a wavelength about 400 nm to about 600 nm, but it will be appreciated that the scope of the instant disclosure and/or claimed subject matter is not intended to be limited to such a range.

Furthermore, a thickness of the scintillator 310 may be dependent upon a desirable or acceptable spread function of the luminescent photons 324. The spread function refers to the distribution of luminescent photons 324 through the scintillator 310. For example, a thickness of the scintillator 310 may be greater if a wide spread function is acceptable (e.g., such as in applications where is it acceptable for luminescent photons 324 generated above a target photodetector to be detected by a second or third order neighbor of the target photodetector) than if a merely a narrower spread function is acceptable (e.g., such as in applications where it is desirable to limit a spread of luminescent photons 324 generated above the target photodetector to merely the target photodetector and immediately adjacent (e.g., first order) photodetectors).

In contrast with the detector array 200 illustrated in FIG. 2, little to no reflective material 312 is situated between the detector elements 302 of the detector array 300. Rather, the reflective material 312 is situated merely around an outer perimeter of the scintillator 310 to trap light within the scintillator 310 and/or to reflect light toward the photodetectors 314. Thus, when a luminescent photon 324 impinges (e.g., interacts with) the scintillator 310 of a detector element 302, such as at the third detector element 302c, luminescent photons 324 generated isotropically may be detected by the second photodetector 314b. There is little to no reflective material 312 to inhibit luminescent photons 324 from traveling between detector elements 302, but a lateral spread of the luminescent photons may be mitigated by the translucent nature of the scintillator material.

The photodetectors 314 are configured to generate electrical charge in response to being exposed to light (e.g., based upon the photovoltaic effect of the photodetector 314). The photodetectors 314 can be constructed of silicon and/or any other photodetector material known to those skilled in the art. For example, in one embodiment, the photodetectors 314 can be made of a high-resistivity silicon wafer, between about 250 μm to 500 μm thick, and is manufactured using planar technology known to those skilled in the art. In some embodiments, the photodetectors 314 comprise silicon pin photodiodes. The photodetectors 314 can be separate single channel devices, or multiple 1D or 2D arrays of photodetectors formed on a monolithic silicon wafer, for example.

Figure 4:
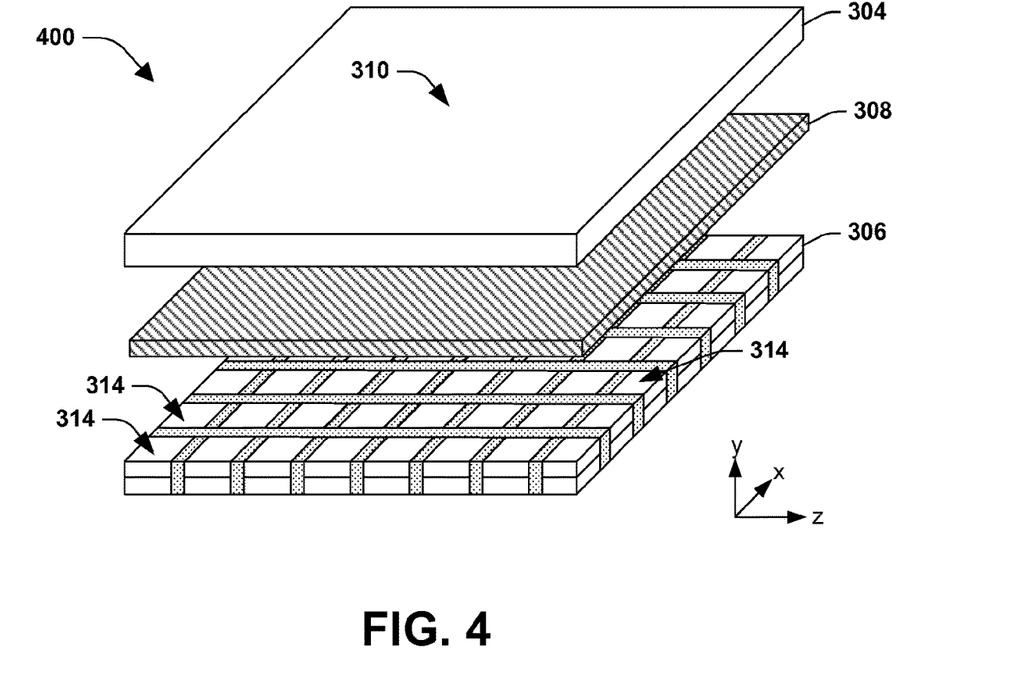
FIG. 4 is a perspective view of an example detector array.
Figure 5:
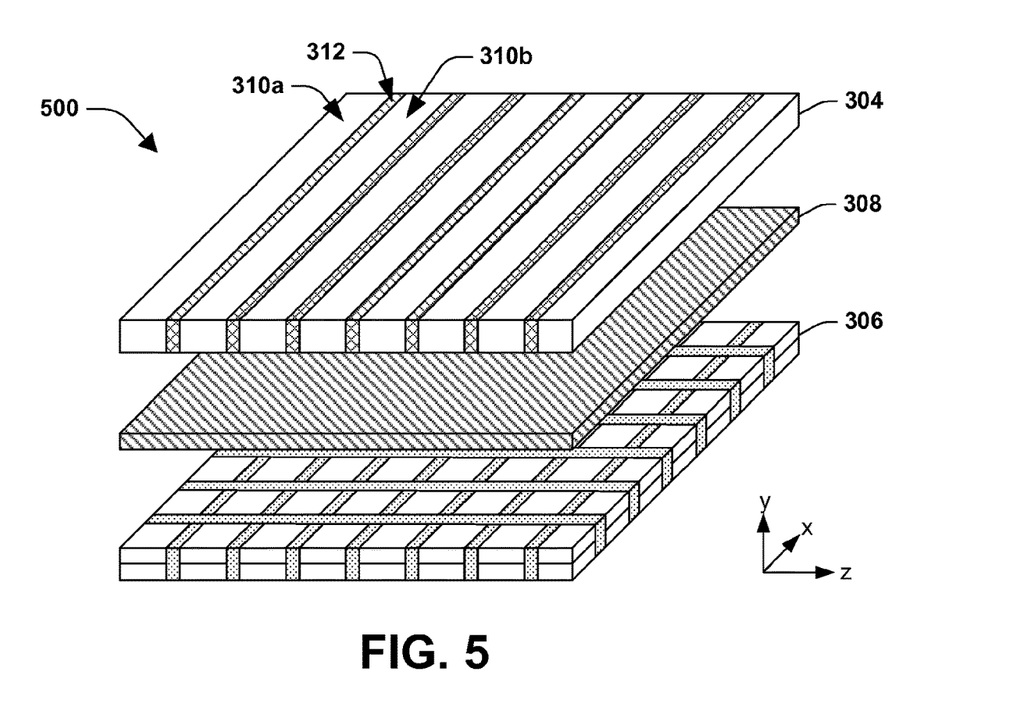
FIG. 5 is a perspective view of an example detector array.
Figure 6:
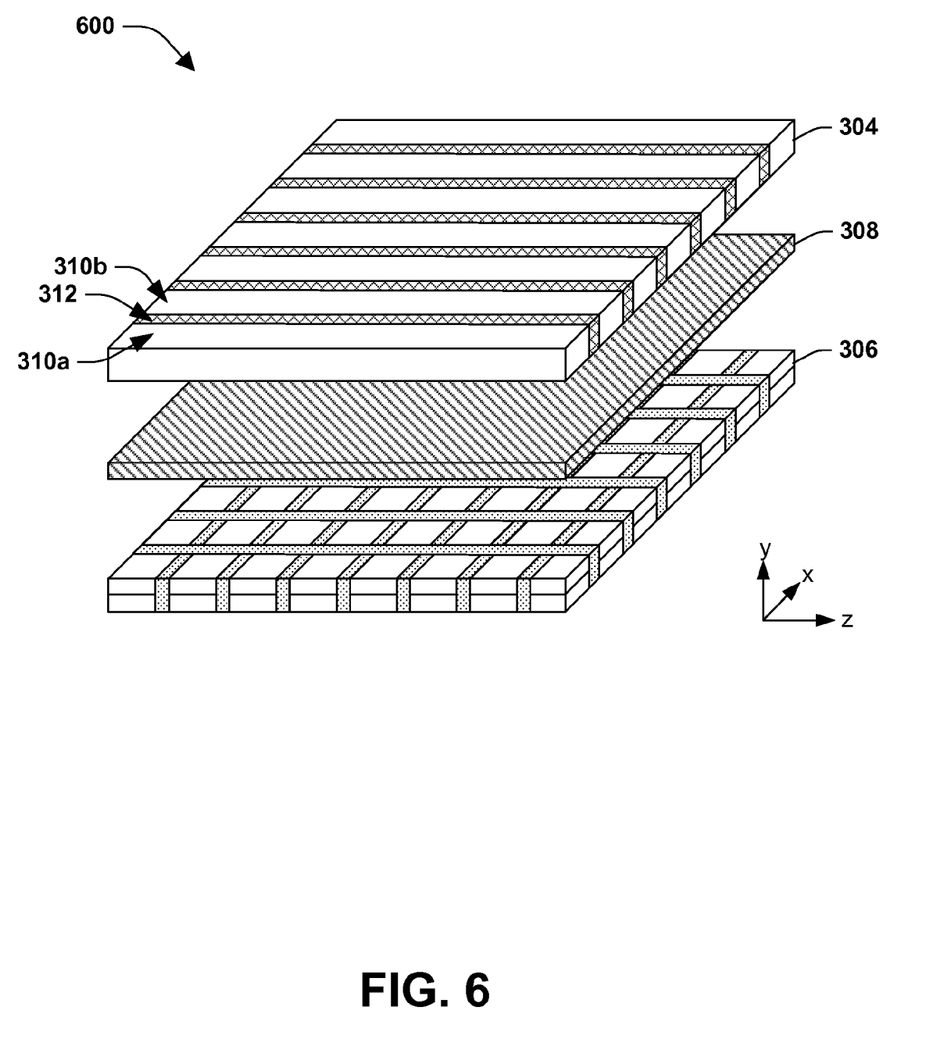
FIG. 6 is a perspective view of an example detector array.

Referring to FIGS. 4-6, perspective views of example detector arrays 400, 500, and 600 according to some embodiments is illustrated. The detector arrays 400, 500, and 600 have been decomposed by layer to further illustrate the layout of respective components within the layer. An upper portion of a reflective material 312 (e.g., situated between the radiation source and a scintillator 310) has been removed from the conversion layer 304 to further illustrate the layout of the scintillator 310.

Referring to FIG. 4, a first example configuration of a detector array 400 according to some embodiments is illustrated. According to this example, the detector array 400 comprises a single scintillator 310 that overlays substantially all photodetectors 314 of the detector array 400.

Referring to FIG. 5, a second example configuration of a detector array 500 according to some to embodiments is illustrated. According to this example, respective columns of detector elements share a scintillator 310. For example, a first column of detector elements share a first scintillator 310a and a second column of detector elements share a second scintillator 310b. Reflective material 312 may be situated between the first scintillator 310a and the second scintillator 310b to mitigate a flow of luminescent photons between columns of detector elements.

Referring to FIG. 6, a third example configuration of a detector array 600 according to some to embodiments is illustrated. According to this example, respective rows of detector elements share a scintillator 310. For example, a first row of detector elements share a first scintillator 310a and a second row of detector elements share a second scintillator 310b. Reflective material 312 may be situated between the first scintillator 310a and the second scintillator 310b to mitigate a flow of luminescent photons 324 between rows of detector elements.

It may be appreciated that due to lack of reflective material between detector elements, optical cross-talk may occur between detector elements. That is, a detector element neighboring a detector element where a detection event occurred may detect at least some luminescent photons generated in response to the detection event because there is little to no reflective material to inhibit luminescent photons from moving laterally between detector elements. To correct for such cross-talk, the data acquisition component 122 and/or image generation component 124 may comprise a high-pass filter or other filter configured to manipulate the data yielded from a first detector element based upon the data yielded from a second detector element neighboring the first detector element. For example, it may be determined that approximately 4% of the luminescent photons generated in response to detection events at the first detector element are detected by the second detected element. Accordingly, a measurement of the electrical charge detected at the first detector element may be acquired and 4% of the measurement may be subtracted from a corresponding measurement of electrical charge detected at the second detector element. In this way, optical cross-talk is corrected post signal generation, for example.

It may also be appreciated that the detector array having one or more detector elements in which a scintillator is shared may have numerous benefits over a conventional detector array as illustrated in FIG. 2. For example, geometric efficiency is improved because radiation impinging a portion of a scintillator above a gap between photodetectors is converted to luminescent photons and thus treated as a detection event (e.g., whereas in the conventional detector array, radiation impinging the reflective material would not be detected). As another example, image aliasing artifacts may be reduced because the shared detector design has a smoother optical impulse response (e.g., which may be substantially parabolic as compared to a box-car optical impulse response of a conventional detector array). The smoother optical impulse response may be closer to an ideal anti-aliasing filter response and thus reduce image aliasing artifacts. As yet another example, manufacturing cost for the detector array may be reduced because the detector array comprises fewer scintillators (e.g., thus requiring fewer dices or cuts).

Although the subject matter has been described in language specific to structural features or methodological acts, it is to be understood that the subject matter of the appended claims is not necessarily limited to the specific features or acts described above. Rather, the specific features and acts described above are disclosed as embodiment forms of implementing at least some of the claims.

Various operations of embodiments are provided herein. The order in which some or all of the operations are described should not be construed to imply that these operations are necessarily order dependent. Alternative ordering will be appreciated given the benefit of this description. Further, it will be understood that not all operations are necessarily present in each embodiment provided herein. Also, it will be understood that not all operations are necessary in some embodiments.

Moreover, "exemplary" is used herein to mean serving as an example, instance, illustration, etc., and not necessarily as advantageous. As used in this disclosure, "or" is intended to mean an inclusive "or" rather than an exclusive "or". In addition, "a" and "an" as used in this disclosure are to generally be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used, such terms are intended to be inclusive in a manner similar to the term "comprising". The claimed subject matter may be implemented as a method, apparatus, or article of manufacture (e.g., as software, firmware, hardware, or any combination thereof).

As used in this disclosure, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc. for features, elements, items, etc. For example, a first channel and a second channel generally corresponds to channel A and channel B or two different or two identical channels or the same channel.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component that performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:
1. A detector array, comprising:
   a scintillator configured to generate luminescent photons responsive to a detection event;
   a plurality of photodetectors situated proximate an underside of the scintillator and configured to detect at least some of the luminescent photons, the scintillator sub- stantially continuously distributed over at least two photodetectors of the plurality; and a reflective material around a perimeter of the scintillator.

2. The detector array of claim 1, wherein the first photodetector of the at least two photodetectors is separated from the second photodetector of the at least two photodetectors by a gap, and wherein the scintillator is substantially continuously distributed over the first photodetector, the gap, and the second photodetector.

3. The detector array of claim 1, wherein there is no reflective material between a first portion of the scintillator over a first photodetector of the at least two photodetectors and a second portion of the scintillator over a second photodetector of the at least two photodetectors.

4. The detector array of claim 1, wherein the scintillator comprises a Gadolinium Oxysulfide (GOS) ceramic material.

5. The detector array of claim 1, wherein the scintillator is bonded to the at least two photodetectors.

6. The detector array of claim 1, wherein the scintillator is substantially continuously distributed over at least three photodetectors, wherein:

the first photodetector of the at least three photodetectors and the second photodetector of the at least three photodetectors form a row of photodetectors, and the first photodetector and a third photodetector of the at least three photodetectors form a column of photodetectors.

7. A detector array, comprising:

a scintillator configured to generate luminescent photons responsive to a detection event; and a plurality of photodetectors situated proximate an underside of the scintillator and configured to detect at least some of the luminescent photons, wherein the plurality of photodetectors comprises rows of photodetectors and columns of photodetectors, wherein the photodetectors of at least a first row of the rows of photodetectors share the scintillator and a second row of the rows of photodetectors share another scintillator.

8. The detector array of claim 7, wherein the scintillator is bonded to the at least two photodetectors.

9. The detector array of claim 7, further comprising a reflective material located between the first row of photodetectors and the second row of photodetectors.

10. The detector array of claim 7, wherein the scintillator comprises an optically translucent material.

11. The detector array of claim 7, wherein the scintillator comprises a Gadolinium Oxysulfide (GOS) ceramic material.

12. The detector array of claim 7, wherein the scintillator comprises a ceramic material.

13. The detector array of claim 7, wherein the scintillator comprises a substantially uniform composition.

14. The detector array of claim 7, wherein the scintillator is devoid of one or more dice-lines between the at least two photodetectors.

15. The detector array of claim 7, further comprising a data acquisition component configured to measure electrical charge generated by the plurality of photodetectors in response to detecting at least some of the luminescent photons.

16. The detector array of claim 7, wherein there is no reflective material between a first portion of the scintillator over a first photodetector of the at least two photodetectors and a second portion of the scintillator over a second photodetector of the at least two photodetectors, further comprising a reflective material disposed around a perimeter of the scintillator.

17. A radiation imaging system, comprising:

a radiation source configured to emit radiation photons;

a detector array comprising a plurality of detector elements comprising rows of detector elements and columns of detector elements, wherein each row of the rows of detector elements share a scintillator or each column of the columns of detector elements share a scintillator; and a reflective material extending between a first shared scintillator and a second shared scintillator.

18. The radiation imaging system of claim 17, wherein a gap is defined between a first photodetector and a second photodetector.

19. The radiation imaging system of claim 18, wherein the first shared scintillator and the second shared scintillator each comprise a substantially same composition of material.

20. The radiation imaging system of claim 17, wherein the radiation source comprises an ionizing radiation source.

* * * * *

UNITED STATES PATENT AND TRADEMARK OFFICE
CERTIFICATE OF CORRECTION

PATENT NO. : 10,539,687 B2
APPLICATION NO. : 15/519569
DATED : January 21, 2020
INVENTOR(S) : Ruvin Deych, Andrew Litvin and Vladan Ristanovic It is certified that error appears in the above-identified patent and that said Letters Patent is hereby corrected as shown below:

In the Specification
Column 6,   Line 58,   change "$320b$" to --$302b$--

Signed and Sealed this
Twenty-fifth Day of February, 2020

Andrei Iancu
*Director of the United States Patent and Trademark Office*